United States Patent
Sakaki et al.

(10) Patent No.: US 11,802,867 B2
(45) Date of Patent: *Oct. 31, 2023

(54) CARDIAC TROPONIN ASSAY METHOD AND ASSAY REAGENT

(71) Applicant: FUJIREBIO INC., Tokyo (JP)

(72) Inventors: Mizuho Sakaki, Hachioji (JP); Yoshiyuki Kitamura, Hachioji (JP); Shintaro Yagi, Hachioji (JP); Katsumi Aoyagi, Hachioji (JP)

(73) Assignee: FUJIREBIO INC., Tokyo (JP)

( * ) Notice: Subject to any disclaimer, the term of this patent is extended or adjusted under 35 U.S.C. 154(b) by 563 days.

This patent is subject to a terminal disclaimer.

(21) Appl. No.: 16/332,647

(22) PCT Filed: Sep. 12, 2017

(86) PCT No.: PCT/JP2017/032793
§ 371 (c)(1),
(2) Date: Mar. 12, 2019

(87) PCT Pub. No.: WO2018/051965
PCT Pub. Date: Mar. 22, 2018

(65) Prior Publication Data
US 2021/0215680 A1 Jul. 15, 2021

(30) Foreign Application Priority Data

Sep. 13, 2016 (JP) ................. 2016-178919

(51) Int. Cl.
*G01N 33/53* (2006.01)
*G01N 33/68* (2006.01)

(52) U.S. Cl.
CPC ..... *G01N 33/5306* (2013.01); *G01N 33/6887* (2013.01)

(58) Field of Classification Search
CPC . G01N 33/53; G01N 33/5306; G01N 33/6887
See application file for complete search history.

(56) References Cited

U.S. PATENT DOCUMENTS

| | | | |
|---|---|---|---|
| 6,114,180 A | 9/2000 | Doth et al. | |
| 6,607,891 B1 | 8/2003 | Takada | |
| 8,546,075 B2 * | 10/2013 | Aoyagi | G01N 33/5767 435/5 |
| 2007/0015218 A1 * | 1/2007 | Cao | G01N 33/537 435/7.2 |
| 2007/0082410 A1 | 4/2007 | Laird et al. | |
| 2008/0044807 A1 * | 2/2008 | Aoyagi | G01N 33/5767 435/5 |
| 2009/0176252 A1 * | 7/2009 | Kojima | A61P 3/00 435/7.9 |
| 2010/0112709 A1 | 5/2010 | Seiki et al. | |
| 2013/0330841 A1 | 12/2013 | Okamura | |
| 2021/0215722 A1 * | 7/2021 | Yamamoto | G01N 33/78 |

FOREIGN PATENT DOCUMENTS

| | | |
|---|---|---|
| EP | 2 144 063 A1 | 1/2010 |
| JP | 2000-241429 A | 9/2000 |
| JP | 5864530 B2 | 2/2016 |
| WO | WO 2006/116005 A2 | 11/2006 |
| WO | WO 2008/126780 A1 | 10/2008 |
| WO | WO 2014/122973 A1 | 8/2014 |
| WO | WO 2016/005328 A2 | 1/2016 |

OTHER PUBLICATIONS

Lippi et al., "Interference from heterophilic antibodies in troponin testing. Case report and systematic review of the literature," Clin. Chim. Acta, 2013, vol. 426, pp. 79-84.*
Eriksson et al., "Comparison of Cardiac Troponin I Immunoassays Variably Affected by Circulating Autoantibodies," Clin. Chem., 2005, vol. 51, issue 5, pp. 848-855.*
Extended European Search Report dated March 4. 2020, in European Patent Application No. 17850867.7.
Greaser, M. L. and J. Gergely, "Reconstitution of Troponin Activity from Three Protein Components;" The Journal of Biological Chemistry (Jul. 10, 1971), vol. 246, No. 13, pp. 4226-4233.
International Search Report (PCT/ISA/210) issued in PCT/JP2017/032793, dated Dec. 19, 2017.
Written Opinion of the International Searching Authority (PCT/ISA/237) issued in PCT/JP2017/032793, dated Dec. 19, 2017.

* cited by examiner

*Primary Examiner* — Galina M. Yakovleva
(74) *Attorney, Agent, or Firm* — Birch, Stewart, Kolasch & Birch, LLP

(57) ABSTRACT

A measurement method and a measurement reagent for cardiac troponin which enable accurate measurement of the amount of cardiac troponin contained in a sample irrespective of the type of the sample and the presence or absence of other components are disclosed. The measurement method for cardiac troponin, wherein cardiac troponin in a sample separated from a body is measured by an immunoassay, includes a pretreatment step of mixing the sample separated from a body with a pretreatment liquid containing one or both of a surfactant and an acidifier. The reagent for immunoassay of cardiac troponin includes a pretreatment liquid containing one or both of a surfactant and an acidifier.

11 Claims, 2 Drawing Sheets
Specification includes a Sequence Listing.

SEQUENCE LISTING

<160> NUMBER OF SEQ ID NOS: 1

<210> SEQ ID NO 1
<211> LENGTH: 210
<212> TYPE: PRT
<213> ORGANISM: Homo sapiens

<400> SEQUENCE: 1

Met Ala Asp Gly Ser Ser Asp Ala Ala Arg Glu Pro Arg Pro Ala Pro
1               5                   10                  15

Ala Pro Ile Arg Arg Arg Ser Ser Asn Tyr Arg Ala Tyr Ala Thr Glu
            20                  25                  30

Pro His Ala Lys Lys Lys Ser Lys Ile Ser Ala Ser Arg Lys Leu Gln
            35                  40                  45

Leu Lys Thr Leu Leu Leu Gln Ile Ala Lys Gln Glu Leu Glu Arg Glu
    50                  55                  60

Ala Glu Glu Arg Arg Gly Glu Lys Gly Arg Ala Leu Ser Thr Arg Cys
65                  70                  75                  80

Gln Pro Leu Glu Leu Ala Gly Leu Gly Phe Ala Glu Leu Gln Asp Leu
            85                  90                  95

Cys Arg Gln Leu His Ala Arg Val Asp Lys Val Asp Glu Glu Arg Tyr
            100                 105                 110

Asp Ile Glu Ala Lys Val Thr Lys Asn Ile Thr Glu Ile Ala Asp Leu
            115                 120                 125

Thr Gln Lys Ile Phe Asp Leu Arg Gly Lys Phe Lys Arg Pro Thr Leu
    130                 135                 140

Arg Arg Val Arg Ile Ser Ala Asp Ala Met Met Gln Ala Leu Leu Gly
145                 150                 155                 160

Ala Arg Ala Lys Glu Ser Leu Asp Leu Arg Ala His Leu Lys Gln Val
            165                 170                 175

Lys Lys Glu Asp Thr Glu Lys Glu Asn Arg Glu Val Gly Asp Trp Arg
            180                 185                 190

Lys Asn Ile Asp Ala Leu Ser Gly Met Glu Gly Arg Lys Lys Lys Phe
    195                 200                 205

Glu Ser
    210

US 11,802,867 B2

CARDIAC TROPONIN ASSAY METHOD AND ASSAY REAGENT

TECHNICAL FIELD

The present invention relates to a measurement method and a measurement reagent for cardiac troponin.

BACKGROUND ART

Cardiac troponin is involved in regulation of myocardial contraction, and present as a complex constituted by three kinds of subunits: cardiac troponin I, troponin C, and cardiac troponin T. Both cardiac troponin I and cardiac troponin T are expressed specifically in the heart, and released into blood when cardiomyocytes are injured. They are therefore used as blood markers in diagnosis of myocardial infarction and monitoring of heart diseases.

The following have been reported as techniques related to measurement of cardiac troponin.

Patent Document 1 describes that stabilization of cardiac troponin in a standard solution is possible by use of a matrix containing a prescribed anionic surfactant (alkyl group having one sulfonate group). Patent Document 2 describes that a divalent cation can be used in immunoassay of cardiac troponin.

PRIOR ART DOCUMENTS

Patent Documents

[Patent Document 1] WO 2006/116005
[Patent Document 2] JP 5864530 B

SUMMARY OF THE INVENTION

Problems to be Solved by the Invention

Blood cardiac troponin is widely used as a diagnostic marker for myocardial infarction. In blood, it is present as a complex composed of cardiac troponin I, troponin C, and cardiac troponin T, and also forms a complex with blood components. In particular, cardiac troponin I easily changes its properties depending on conditions of other components and the like. For example, it shows interaction with heparin in the presence of heparin, and is easily degraded by blood protease. Thus, since cardiac troponin I does not show stable values in immunoassays using anti-troponin antibodies, it has been regarded as an instable protein. For example, in some cases, a measured value of cardiac troponin I obtained using serum as a blood sample is not necessarily the same as a measured value of cardiac troponin I obtained using plasma as a blood sample. In clinical sites, blood collection tubes containing various anticoagulants (for example, heparin, EDTA, and citric acid) are used for preparation of plasma. The measured value of cardiac troponin I in plasma may vary depending on the type of the anticoagulant used for the preparation of the plasma. Furthermore, measurement reagents using different antibodies for the detection show deviations of the measured value of troponin. Thus, in diagnosis of myocardial infarction based on measurement of the amount of cardiac troponin I, the true value of cardiac troponin I cannot be easily determined by an immunoassay, and it is therefore difficult to set a particular normal value that is not influenced by the type of the sample or by other components, which is problematic. Regarding measurement of cardiac troponin T, the problem of deviation of the measured value, as is seen for troponin I, is relatively small since a single measurement method is used. However, there is a possibility that the same problem as in the case of cardiac troponin I may occur when a plurality of measurement methods are reported in the future.

An object of the present invention is to provide a measurement method and a measurement reagent for cardiac troponin which enable more accurate measurement of the amount of cardiac troponin contained in a sample irrespective of the type of the sample and the presence or absence of other components.

Means for Solving the Problems

As a result of intensive study to achieve the above object, the present inventors discovered that, in use of a method for immunologically measuring cardiac troponin I in a biological sample, a highly reproducible measured value of cardiac troponin can be obtained by carrying out, before subjecting the biological sample to an immune reaction, a pretreatment step of mixing with a pretreatment liquid containing one or both of a surfactant and an acidifier, irrespective of the type of the biological sample and the presence or absence of other components, thereby completing the present invention.

The present invention has the following constitution.
(1) A method of measuring, by immunoassay, cardiac troponin in a sample separated from a body, the method comprising a pretreatment step of mixing the sample separated from a body with a pretreatment liquid containing one or both of a surfactant and an acidifier.
(2) The method according to (1), wherein the pretreatment liquid further contains a reducing agent.
(3) The method according to (1) or (2), wherein the pretreatment liquid contains a surfactant, and the surfactant is one or more selected from the group consisting of anionic surfactants, cationic surfactants, zwitterionic surfactants, and nonionic surfactants.
(4) The method according to (3), wherein the surfactant is an anionic surfactant.
(5) The method according to (3), wherein the pretreatment step is carried out under heat.
(6) The method according to (1), wherein the pretreatment liquid contains an acidifier, and the acidifier has a final concentration of more than 0.05 N and not more than 0.5 N in the pretreatment step.
(7) The method according to any one of (1) to (6), wherein the cardiac troponin is cardiac troponin I.
(8) A reagent for immunoassay of cardiac troponin, the reagent comprising a pretreatment liquid containing one or both of a surfactant and an acidifier.

Effect of the Invention

According to the present invention, by releasing cardiac troponin from other components to reduce the influence of interactions, a measurement method and a measurement reagent for cardiac troponin which enable accurate measurement of the amount of cardiac troponin contained in a sample irrespective of the type of the sample and the presence or absence of other components can be provided. Further, according to the present invention, by achieving homogeneity of properties of cardiac troponin, a measurement method and a measurement reagent for cardiac troponin which enable stable and sensitive measurement of cardiac troponin can be provided.

MODE FOR CARRYING OUT THE INVENTION

<Measurement Method for Cardiac Troponin>

Figure 1:
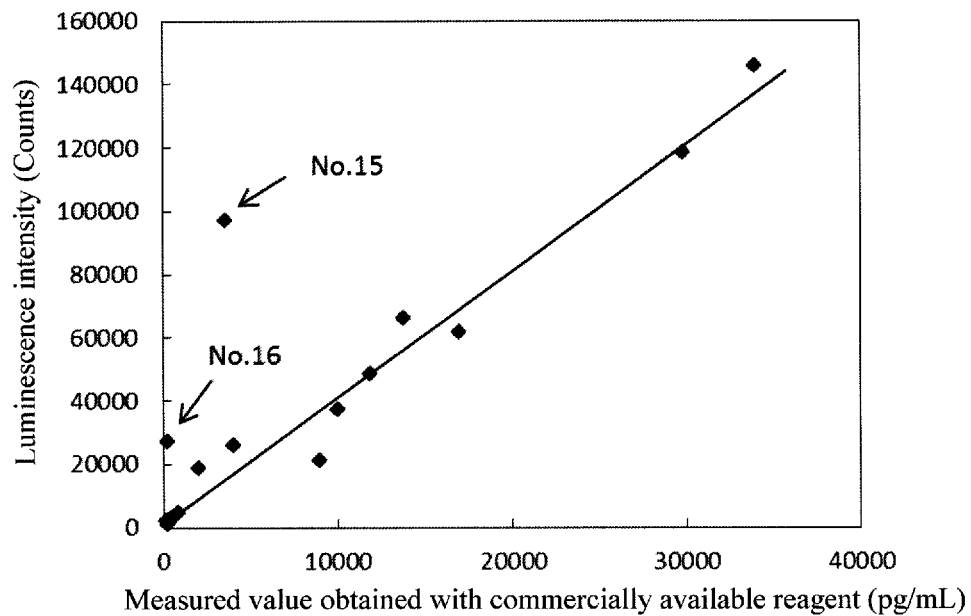
FIG. 1 is a diagram showing correlation between the value of cardiac troponin I in serum measured using a commercially available reagent and the value of cardiac troponin I in serum measured by the measurement method of the present invention using acidification pretreatment.

The cardiac troponin to be measured by the method of the present invention may be any of cardiac troponin I, troponin C, and cardiac troponin T, and is preferably cardiac troponin I. Cardiac troponin I (cTnI) is one of the three kinds of subunits (troponins I, C, and T) constituting the cardiac troponin complex, which is involved in regulation of myocardial contraction. The cardiac troponin to be measured by the present invention is cardiac troponin derived from an arbitrary animal. The cardiac troponin is preferably cardiac troponin derived from a mammal (for example, a primate such as human, monkey, or chimpanzee; a rodent such as mouse, rat, or rabbit; a pet animal such as dog or cat; a domestic animal such as pig or cow; or a working animal such as horse or sheep), more preferably cardiac troponin derived from a primate, especially preferably cardiac troponin derived from human. For an amino acid sequence of cardiac troponin I derived from human, see, for example, GenBank:CAA62301.1. Of course, the cardiac troponin I derived from human is not limited to cardiac troponin I having the amino acid sequence referred by the above number, and may also be a mutant (for example, a naturally occurring mutant) thereof. The cardiac troponin I to be measured by the present invention may be present as a free form, in the form of a complex with troponin C and/or troponin T, or in the form of a complex with another molecule such as an autoantibody, in the biological sample. For an amino acid sequence of troponin C derived from human, see, for example, GenBank:AAA36772.1. For an amino acid sequence of cardiac troponin T derived from human, see, for example, GenBank:CAA52818.1.

1. Pretreatment Step

The method of the present invention is a method in which cardiac troponin I present in a biological sample is measured using immune reaction by reacting the biological sample with an antibody. The method is characterized in that it includes a pretreatment step of mixing the biological sample with a pretreatment liquid before the immune reaction (reaction step). By the pretreatment step, cardiac troponin I can be brought into a free state, so that the influence of interactions with other components such as proteins can be reduced. The pretreatment liquid may contain one of a surfactant and an acidifier, or may contain both of these. The pretreatment liquid preferably contains a surfactant or an acidifier.

The volume ratio between the biological sample and the pretreatment liquid to be mixed in the pretreatment step is preferably 1:10 to 10:1, more preferably 1:5 to 5:1, still more preferably 1:3 to 3:1. The biological sample to be used in the present invention is not limited as long as it is a sample that may contain cardiac troponin I. and examples of the biological sample include serum, plasma, whole blood, urine, stool, oral mucosa, pharyngeal mucosa, intestinal mucosa, and biopsy specimens (for example, intestinal specimens and liver specimens). The biological sample is preferably serum or plasma.

The surfactant to be contained in the pretreatment liquid may be any of an anionic surfactant, cationic surfactant, zwitterionic surfactant, and nonionic surfactant. The surfactant is especially preferably an anionic surfactant. Preferred examples of the anionic surfactant include sodium dodecyl sulfate (SDS), sodium N-lauroyl sarcosinate (NLS), lithium dodecyl sulfate, sodium dodecylbenzene sulfonate, and deoxycholic acid. SDS or NLS may be especially preferably used. Examples of the cationic surfactant include hexadecyltrimethylammonium chloride (C16TAC) and hexadecyltrimethylammonium bromide (CTAB). Examples of the zwitterionic surfactant include CHAPS. Examples of the nonionic surfactant include Tween 20 and Triton X-100. The surfactant needs to have a concentration sufficient for releasing of cardiac troponin I from other proteins and the like. The concentration during the pretreatment of the mixed liquid prepared by mixing with the biological sample is preferably 0.1 to 12.5%, more preferably 0.25 to 10%, still more preferably 0.5 to 7.5%. In cases where the surfactant concentration is 0.1 to 12.5%, sufficient release of cardiac troponin I and suppression of precipitation and the like can be effectively achieved.

Preferred examples of the acidifier contained in the pretreatment liquid include hydrochloric acid, sulfuric acid, and acetic acid. The normality of the acid in the pretreatment liquid, in terms of the concentration during the pretreatment, is preferably more than 0 N and not more than 0.5 N, especially preferably 0.03 N to 0.125 N. In cases where an acidifier is used for the pretreatment, a cationic surfactant is preferably added in order to prevent occurrence of precipitation upon mixing with the biological sample. The cationic surfactant is especially preferably a cationic surfactant having, in a single molecule, a single-chain alkyl group having or more carbon atoms, and a tertiary amine or a quaternary ammonium salt. Examples of such a surfactant include decyltrimethylammonium chloride, dodecyltrimethylammonium chloride, tetradecyltrimethylammonium chloride, hexadecyltrimethylammonium chloride (C16TAC), decyltrimethylammonium bromide, dodecyltrimethylammonium bromide, tetradecyltrimethylammonium bromide, hexadecyltrimethylammonium bromide (CTAB), laurylpyridinium chloride, tetradecylpyridinium chloride, and cetylpyridinium chloride. The amount of the cationic surfactant to be added, in terms of the concentration after mixing with the sample, is preferably 0.01% to 15%, more preferably 0.05% to 10%.

A reducing agent is also preferably used for the pretreatment liquid. As the reducing agent, any of known reducing agents such as 2-(diethylamino)ethanethiol hydrochloride (DEAET), tris(2-carboxyethyl)phosphine hydrochloride (TCEP), dithiothreitol (DTT), 2-mercaptoethanol, thioglycerol, sodium sulfite, and borohydride may be used. From the viewpoint of stability in the solution, DEAET or TCEP may be especially preferably used. The concentration of the reducing agent, in terms of the concentration during the pretreatment, is preferably 0.1 to 200 mM, more preferably 0.5 to 100 mM, still more preferably 1.0 to 40.0 mM.

When necessary, the pretreatment liquid may contain another protein denaturant such as urea or thiourea. The concentration of the denaturant, in terms of the concentration during the treatment, is preferably not less than 0.1 M, more preferably not less than 0.5 M and less than 4 M. For enhancement of the effect of the treatment, the pretreatment liquid may contain either a monosaccharide or a disaccharide, or a combination of both of these. The pretreatment liquid may also contain a chelating agent. Cardiac troponin I is known to easily cause interaction with troponin C and the like in the presence of a divalent cation such as calcium ion. By the use of the chelating agent, the influence of calcium ions and the like can be avoided, and easier release of cardiac troponin I can be achieved. As the chelating agent, any of EDTA, citric acid, EGTA, phytic acid, and the like may be used. EDTA is especially preferably used.

In the pretreatment step, the mixing of the biological sample with the pretreatment liquid is preferably further followed by heating. In particular, in cases where a surfactant is used for the pretreatment liquid, heating is preferably carried out in order to increase its effect. The heating temperature is preferably 35 to 95° C., more preferably 50 to 90° C., still more preferably 70 to 85° C. The heating time is preferably not less than 1 minute, more preferably not less than 3 minutes, still more preferably not less than 5 minutes. There is no upper limit of the heating time. The heating time may be usually not more than 60 minutes, especially preferably not more than 30 minutes.

The pretreatment step may also have, after the mixing of the biological sample with the pretreatment liquid, a neutralization process of adding and mixing a neutralization liquid. In particular, in cases where an acidifier is used for the pretreatment liquid, it is useful to carry out the neutralization process before the reaction step (antigen-antibody reaction) in order to adjust the pH of the mixed liquid to a condition suitable for the reaction. As the neutralization liquid, a solution containing an alkalizer such as sodium hydroxide or potassium hydroxide, or a pH buffer such as bicine or tricine may be preferably used. The neutralization liquid may also contain a surfactant such as SDS or NLS.

2. Reaction Step

The biological-sample-mixed liquid obtained by the pretreatment step in the method of the present invention is subsequently subjected to the reaction step of immunoassay. In the reaction step, the biological-sample-mixed liquid is mixed with a buffer, and antigen in the mixed liquid is allowed to react with an antibody against cardiac troponin.

Examples of the buffer include those based on MES buffer, phosphate buffer, citrate buffer, Tris buffer, or carbonate buffer. Buffers based on phosphate buffer or citrate buffer may be especially preferably used. The buffer may also contain a chelating agent such as EDTA for maintaining the effect of the pretreatment. In cases where a pretreatment liquid containing a surfactant is used, for example, a buffer containing a water-soluble polymer such as BSA, polyvinyl pyrrolidone (PVP), polyvinyl alcohol (PVA), or dextran sulfate sodium at about 0.01 to 10%, especially 0.05 to 5.0% in terms of the final concentration after mixing with the pretreated mixed liquid is preferably used. In cases where a pretreatment liquid containing an acidifier is used, it is preferred to use a buffer containing an alkaline agent or having a buffer capacity capable of decreasing the influence of the acid in the pretreatment liquid. The mixed liquid of the pretreatment step and the buffer are mixed at a volume ratio of preferably 1:10 to 10:1, more preferably 1:5 to 5:1, still more preferably 1:3 to 3:1.

The antibody against cardiac troponin to be used in the method of the present invention is an antibody that recognizes at least part of the amino acid sequence of cardiac troponin as an epitope. As epitopes recognized by antibodies against cardiac troponin I, various epitopes including specific epitopes are known (for example, Filatov vl et al., Biochem. Mol. Biol. Int. 1998, 45(6): 1179-1187; WO 2012/115221). Thus, the antibody against cardiac troponin I is not limited, and its examples include antibodies that recognize such a variety of epitopes. Preferably, an antibody having a property which allows recognition of free cardiac troponin I may be used. In particular, an antibody whose reactivity to free (simple) cardiac troponin I is higher than reactivity to cardiac troponin forming a complex is preferred. Examples of the epitopes of such antibodies include a region overlapping with the binding site for troponin C (43rd to 65th amino acid residues), and parts of this region. The examples also include a region overlapping with the binding site for cardiac troponin T (66th to 89th), and parts of this region. Since such epitope regions are present in the inside of the complex in a normal sample, they are less likely to be degraded, and can be stably present. The amino acid positions in cardiac troponin I protein in the present description are based on the amino acid sequence described in GenBank:CAA62301.1 (SEQ ID NO:1).

The antibody against cardiac troponin I may be a commercially available antibody that can be easily obtained. Examples of the epitope in the amino acid sequence of human-derived cardiac troponin I include epitopes found in the peptide portion composed of the 20th to 60th amino acid residues (for example, the peptide composed of the 24th to 40th or 41st to 49th amino acid residues), epitopes found in the peptide portion composed of the 61st to 120th amino acid residues (for example, the peptide composed of the 86th to 90th amino acid residues), epitopes found in the peptide portion composed of the 130th to 150th amino acid residues, and epitopes found in the peptide portion composed of the 160th to 209th amino acid residues. Preferably, the antibody against cardiac troponin I is an antibody that recognizes an epitope specific to cardiac troponin I (especially an epitope specific to human cardiac troponin I).

The antibody against cardiac troponin may be either a polyclonal antibody or a monoclonal antibody. The antibody against cardiac troponin may be any isotype of immunoglobulins (for example, IgG, IgM, IgA, IgD, IgE, or IgY). The antibody against cardiac troponin may be a full-length antibody. The full-length antibody means an antibody containing a heavy chain and a light chain each having a variable region and a constant region (for example, an antibody containing two Fab portions and an Fc portion). The antibody against cardiac troponin may also be an antibody fragment derived from such a full-length antibody. The antibody fragment is part of a full-length antibody, and examples of the antibody fragment include antibodies lacking the constant region (for example, F(ab')2, Fab', Fab, or Fv). The antibody against cardiac troponin may also be a modified antibody such as a single-chain antibody.

The antibody against cardiac troponin can be prepared using a conventionally known method. For example, the antibody against cardiac troponin can be prepared using the above-described epitope as an antigen. Alternatively, since a number of antibodies against cardiac troponin that recognize the above-described epitopes are commercially available, such commercially available products may also be used.

The antibody against cardiac troponin may be immobilized on a solid phase. In the present description, an antibody immobilized on a solid phase may be simply referred to as an immobilized antibody. Examples of the solid phase include solid phases in which a liquid phase can be stored or loaded (for example, supports such as plates, membranes, and test tubes; and containers such as well plates, microchannels, glass capillaries, nanopillars, and monolith columns) and solid phases that can be suspended or dispersed in a liquid phase (for example, solid-phase carriers such as particles). Examples of the material of the solid phase include glasses, plastics, metals, and carbons. As the material of the solid phase, a non-magnetic material or a magnetic material may be used. From the viewpoint of simplicity of operation and the like, the material is preferably a magnetic material. The solid phase is preferably a solid-phase carrier, more preferably a magnetic solid-phase carrier, still more preferably a magnetic particle. As the method for immobilization of the antibody, a conventionally known method may be used. Examples of such a method include physical adsorption, covalent bonding, use of an affinity substance (biotin, streptavidin, or the like), and ionic bonding. In a particular embodiment, the antibody against cardiac troponin is an antibody immobilized on a solid phase, preferably an antibody immobilized on a magnetic solid phase, more preferably an antibody immobilized on a magnetic particle.

In the reaction step, after the mixing of the mixed liquid of the pretreatment step with the buffer, the resulting mixture may be brought into contact with the immobilized antibody, or, for example, an antibody immobilized on particles may be preliminarily included in a buffer to provide a particle liquid followed by mixing the above mixed liquid with the particle liquid. Although the reaction step may be carried out by a primary reaction step alone as in the immunoagglutination method or the competitive method, a secondary reaction step may also be provided. In cases where the secondary reaction step is provided, a washing step for removal of unreacted components may be provided between the primary reaction step and the secondary reaction step.

The antibody against cardiac troponin may be labeled with a labeling substance. In the present description, an antibody labeled with a labeling substance may be simply referred to as a labeled antibody. Examples of the labeling substance include enzymes (peroxidase, alkaline phosphatase, luciferase, β-galactosidase, and the like), affinity substances (streptavidin, biotin, and the like), fluorescent substances and proteins (fluorescein, fluorescein isothiocyanate, rhodamine, green fluorescent protein, red fluorescent protein, and the like), luminescent or light-absorbing substances (luciferin, aequorin, acridinium, ruthenium, and the like), and radioactive substances ($^3$H, $^{14}$C, $^{32}$P, $^{35}$S, $^{125}$I, and the like). In cases where the secondary reaction is provided in the method of the present invention, the antibody to be used for the secondary reaction may be labeled with such a labeling substance.

In a particular embodiment, the antibody to be used for the secondary reaction in the method of the present invention includes another antibody against cardiac troponin that recognizes an epitope different from that of the above antibody against cardiac troponin. Details of such an epitope recognized by the other antibody are the same as the details of the epitope of the above-described antibody against cardiac troponin (however, in the case of combined use, the types of the epitopes are different). The combination of the epitope recognized by the antibody against cardiac troponin and the epitope recognized by the other antibody against cardiac troponin is not limited. For example, in cases where an antibody that recognizes a particular epitope found in the peptide portion composed of the 20th to 60th amino acid residues (for example, the peptide composed of the 24th to 40th or 41st to 49th amino acid residues) is used as the antibody against cardiac troponin I, an antibody that recognizes an epitope other than the particular epitope, for example, another epitope found in the peptide portion composed of the 20th to 60th amino acid residues (for example, the peptide composed of the 24th to 40th or 41st to 49th amino acid residues), an epitope found in the peptide portion composed of the 61st to 120th amino acid residues (for example, the peptide composed of the 86th to 90th amino acid residues), an epitope found in the peptide portion composed of the 130th to 150th amino acid residues, or an epitope found in the peptide portion composed of the 160th to 209th amino acid residues, may be used as the other antibody against cardiac troponin I. Use of such another antibody is preferred in cases where, for example, the sandwich method is used.

3. Detection Step

In cases where a label is used for the primary antibody or the secondary antibody, the detection is carried out by a method suitable for the label used. For example, in cases where an enzyme label is used, the detection is carried out by adding a substrate of the enzyme. For example, in cases where alkaline phosphatase (ALP) is used for the labeled antibody, 3-(2'-spiroadamantane)-4-methoxy-4-(3'-phosphoryloxy)phenyl-1,2-dioxetane disodium salt (AMPPD) may be used as the enzyme substrate to provide a system of the chemiluminescent enzyme immunoassay (CLEIA) method.

The method of the present invention is an immunoassay using an antibody against cardiac troponin. Examples of such an immunoassay include the direct competitive method, indirect competitive method, and sandwich method. Further examples of such an immunoassay include chemiluminescent enzyme immunoassay (CLEIA), chemiluminescence immunoassay (CLIA), turbidimetric immunoassay (TIA), enzyme immunoassay (EIA) (for example, direct competitive ELISA, indirect competitive ELISA, and sandwich ELISA), radioimmunoassay (RIA), latex agglutination, fluoroimmunoassay (FIA), and immunochromatography. These immunoassays per se are well known, and do not need to be described herein in detail. A brief description of each immunoassay is given below.

The direct competitive method is a method in which an antibody against a target antigen to be measured (in the present invention, cardiac troponin I) is immobilized on a solid phase (the solid phase and the immobilization are as described above), and blocking treatment (treatment of the solid phase with a solution of protein such as serum albumin) for prevention of non-specific adsorption is carried out, followed by reacting this antibody with a test sample containing the target antigen (in the present invention, a biological sample subjected to the pretreatment step as described above) and a certain amount of labeled antigen (the label is as described above), performing washing, and then quantifying the label bound to the solid phase. Since the antigen in the test sample and the labeled antigen competitively bind to the antibody, as the amount of the antigen in the test sample increases, the amount of the label bound to the solid phase decreases. Antigen standard solutions with various known concentrations are prepared, and the amount of the label (the absorbance, luminescence intensity, fluorescence intensity, or the like depending on the properties of the label; the same applies hereinafter) immobilized on the solid phase is measured for each solution, followed by preparation of a calibration curve in which the antigen concentration is taken along the abscissa, and the amount of the label is taken along the ordinate. By measuring the amount of the label for an unknown test sample, and applying the measured amount of the label to the calibration curve, the amount of the antigen in the unknown test sample can be measured. The direct competitive method per se is well known in the art, and described in, for example, US 20150166678 A1.

In the indirect competitive method, a target antigen (in the present invention, cardiac troponin I) is immobilized on a solid phase (the solid phase and the immobilization are as described above). Subsequently, blocking treatment of the solid phase is carried out, and then a test sample containing the target antigen (in the present invention, a biological sample subjected to the pretreatment step as described above) is mixed with a certain amount of an anti-target-antigen antibody, followed by reaction with the immobilized antigen. After washing, the anti-target-antigen antibody bound to the solid phase is quantified. This can be carried out by allowing reaction with a labeled secondary antibody (the label is as described above) against the anti-target-antigen antibody, performing washing, and then measuring the amount of the label. Antigen standard solutions with various known concentrations are prepared, and the amount of the label immobilized on the solid phase is measured for each solution, followed by preparation of a calibration curve. By measuring the amount of the label for an unknown test sample, and applying the measured amount of the label to the calibration curve, the amount of the antigen in the unknown test sample can be measured. It is also possible to use a labeled primary antibody without using the labeled secondary antibody. The indirect competitive method per se is well known in the art, and described in, for example, the above-mentioned US 20150166678 A1.

The sandwich method is a method in which an anti-target-antigen antibody is immobilized on a solid phase (the solid phase and the immobilization are as described above), and blocking treatment is carried out, followed by reaction with a test sample containing a target antigen (in the present invention, a biological sample subjected to the pretreatment step as described above), washing, reaction with a labeled secondary antibody against the target antigen (the label is as described above), washing, and then quantification of the label bound to the solid phase. Antigen standard solutions with various known concentrations are prepared, and the amount of the label immobilized on the solid phase is measured for each solution, followed by preparation of a calibration curve. By measuring the amount of the label for an unknown test sample, and applying the measured amount of the label to the calibration curve, the amount of the antigen in the unknown test sample can be measured. The sandwich method per se is well known in the art, and described in, for example, US 20150309016 A1.

Among the immunoassays described above, chemiluminescent enzyme immunoassay (CLEIA), chemiluminescence immunoassay (CLIA), enzyme immunoassay (EIA), radioimmunoassay (RIA), and fluoroimmunoassay (FIA) are immunoassays classified based on the type of the label to be used when the direct competitive method, indirect competitive method, sandwich method, or the like described above is carried out. Chemiluminescent enzyme immunoassay (CLEIA) is an immunoassay which uses an enzyme (for example, the above-described alkaline phosphatase) as a label, and uses a substrate that generates a chemiluminescent compound (for example, the above-described AMPPD) as a substrate. Enzyme immunoassay (EIA) is an immunoassay which uses an enzyme (for example, the above-described peroxidase, alkaline phosphatase, luciferase, or β-galactosidase) as a label. As the substrate of each enzyme, a compound quantifiable by measurement of the absorbance or the like is used. For example, in cases of peroxidase, 1,2-phenylenediamine (OPD), 3,3'5,5'-tetramethylbenzidine (TMB), or the like is used. In cases of alkaline phosphatase, p-nitrophenyl phosphate (pNPP) or the like is used. In cases of β-galactosidase, MG: 4-methylumbelliferyl galactoside, NG: nitrophenyl galactoside, or the like is used. In cases of luciferase, luciferin or the like is used. Radioimmunoassay (RIA) is a method which uses a radioactive substance as a label. Examples of the radioactive substance include radioactive elements such as $^3H$, $^{14}C$, $^{32}P$, $^{35}S$, and $^{125}I$ as described above. Fluoroimmunoassay (FIA) is a method which uses a fluorescent substance or a fluorescent protein as a label. Examples of the fluorescent substance or the fluorescent protein include, as described above, fluorescein, fluorescein isothiocyanate, rhodamine, green fluorescent protein, and red fluorescent protein. Immunoassays per se using these labels are well known in the art, and described in, for example, U.S. Pat. No. 8,039,223 B and US 20150309016 A1.

Turbidimetric immunoassay (TIA) is an immunoassay which utilizes the phenomenon that an antigen-antibody complex produced by antigen-antibody reaction between a target antigen to be measured (in the present invention, cardiac troponin I) and an antibody against this antigen causes an increase in the turbidity. The antigen is added, at various known concentrations, to an anti-target-antigen antibody solution, and the turbidity of each resulting mixture is measured to prepare a calibration curve. By similarly measuring the turbidity of an unknown test sample, and applying the measured turbidity to the calibration curve, the amount of the antigen in the unknown test sample can be measured. Turbidimetric immunoassay per se is well known in the art, and described in, for example, US 20140186238 A1. Latex agglutination is a method similar to turbidimetric immunoassay, but uses a suspension of latex particles whose surfaces have an anti-target-antigen antibody immobilized thereon, instead of the antibody solution in turbidimetric immunoassay. Turbidimetric immunoassay and latex agglutination per se are well known in the art, and described in, for example, U.S. Pat. No. 820,398 B.

Immunochromatography is a method in which the above-described sandwich method or competitive method is carried out on a substrate (also called a matrix or a strip) formed with a porous material such as filter paper, cellulose membrane, glass fiber, or non-woven fabric. For example, in cases of immunochromatography by the sandwich method, a detection zone on which an anti-target-antigen antibody is immobilized is provided on the substrate, and a test sample containing a target antigen (in the present invention, a biological sample subjected to the pretreatment step as described above) is added to the substrate, followed by allowing a developer to flow from the upstream side, thereby allowing the target antigen to migrate to the detection zone and immobilizing the target antigen on the detection zone. The immobilized target antigen is sandwiched with a labeled secondary antibody, and the label immobilized on the detection zone is detected to detect the target antigen in the test sample. By forming a label zone containing the labeled secondary antibody in the upstream side of the detection zone, the conjugate of the target antigen and the labeled secondary antibody can be immobilized on the detection zone. In cases where the label is an enzyme, a substrate zone containing a substrate of the enzyme is also provided in the upstream side of the detection zone. In cases of the competitive method, for example, the target antigen may be immobilized on the detection zone, and the target antigen in the test sample may be allowed to compete with the target antigen immobilized on the detection zone. By providing a labeled antibody zone in the upstream side of the detection zone, allowing the target antigen in the test sample to react with the labeled antibody, immobilizing unreacted labeled antibody on the detection zone, and then detecting or quantifying the label, the target antigen in the test sample can be detected or quantified. Immunochromatography per se is well known in the art, and described in, for example, U.S. Pat. No. 6,210,898 B.

<Measurement Reagent for Cardiac Troponin I>

The measurement reagent for cardiac troponin of the present invention is a measurement reagent that can realize the above-described measurement method for cardiac troponin. The measurement reagent of the present invention is characterized in that it contains, as a constituting component, a pretreatment liquid containing one or both of a surfactant and an acidifier, in addition to the constitution used for ordinary immunoassays.

The reagent of the present invention contains the constituting components in a form in which they are isolated from each other, or in the form of a composition. More specifically, the constituting components may be provided in a form in which they are stored in different containers (for example, tubes or plates), or some of the constituting components may be provided in the form of a composition (for example, in a single solution). Alternatively, the reagent of the present invention may be provided in the form of a device. More specifically, the reagent may be provided in a form in which all constituting components are stored in a device. Alternatively, the reagent may be provided in a form in which some of the constituting components are stored in a device while the remaining constituting components are not stored in the device (for example, in a form in which they are stored in a different container(s)). In such a case, the constituting components not stored in the device may be used by injection into the device upon the measurement of the target substance.

In a preferred embodiment, the reagent of the present invention may have a constitution suitable for the type of the immunoassay to be employed. For example, in cases where the sandwich method is employed, the reagent of the present invention may contain, as indispensable constituting components, i) a pretreatment liquid, ii) an antibody against cardiac troponin I, and iii) a buffer; and, as arbitrary constituting components, iv) another antibody against cardiac troponin I, v) a labeling substance, vi) a diluent, and, when necessary, vii) a substrate that reacts with the labeling substance. The constituting components ii) and iii) may be contained in a single solution. The constituting component iv) may be labeled with the labeling substance v). The antibody against cardiac troponin may be preferably immobilized on a magnetic particle.

EXAMPLES

Example 1 Test for Confirmation of Effect of SDS Pretreatment (1)

(1) Preparation of Anti-Cardiac Troponin I (cTnI) Antibody Plate

To a polystyrene 96-well microwell plate (manufactured by Nunc), an antibody dilution solution (0.1 M sodium hydrogen carbonate, pH 9.6) containing 2 µg/mL anti-cTnI antibody 19C7 (manufactured by Hytest Ltd.) was dispensed at 100 µL/well, and the plate was then incubated at 4° C. overnight. The microwell plate was washed with PBS three times, and then a blocking liquid (PBS containing 0.5% casein sodium, 2% sucrose, and 0.05% ProClin (registered trademark) 300) was dispensed thereto at 350 µL/well, followed by incubation at room temperature for not less than 2 hours. After removing the blocking liquid, the plate was dried to provide an anti-cTnI antibody plate.

(2) Sample Pretreatment

Pretreatment liquids 1 to 3 shown in Table 1 were prepared. Each of two serum samples with known cTnI concentrations or a blank (serum from a healthy individual) was mixed with each of the pretreatment liquids 1 to 3 at a ratio of pretreatment liquid:serum sample=1:2 (volume ratio, the same applies hereinafter), and the resulting mixture was heated at 80° C. for 5 minutes with shaking at 1000 rpm, to provide a treated sample. In addition, PBS was mixed with each serum sample at a ratio of PBS:serum sample=1:2, to provide an untreated sample (without heating). The cTnI concentration in the serum sample was preliminarily measured using Centaur manufactured by Siemens.

(3) Measurement of cTnI in Sample

The treated sample was mixed with a buffer (24 mM potassium dihydrogen phosphate, 76 mM dipotassium hydrogen phosphate, 1.0% BSA, 1.0% PVP, 0.05% casein sodium, 0.05% Tween 20 (trade name), 0.05% sodium chloride, 0.10% Proclin (registered trademark) 300) at a ratio of treated sample:buffer=1:2, and the resulting mixture was added to the anti-cTnI antibody plate at 100 µL/well (primary reaction). After allowing the reaction to proceed with shaking at room temperature for 2 hours, washing was carried out five times with a washing liquid (0.05% Tween 20 (trade name)/PBS). A buffer containing 1 µg/mL biotinylated anti-cTnI antibody 16A11 (Hytest Inc.) was dispensed at 100 µL/well, and the reaction was allowed to proceed with shaking at room temperature for 1 hour (secondary reaction). After five times of washing with the washing liquid, a labeled antibody liquid prepared by 10,000-fold dilution of HRP-labeled streptavidin (manufactured by Roche) with the buffer was dispensed at 100 µL/well, and the reaction was allowed to proceed with shaking at room temperature for 30 minutes. After five times of washing with the washing liquid, OPD substrate liquid (manufactured by Wako Pure Chemical Industries, Ltd.) was dispensed at 100 µL/well, and the plate was left to stand at room temperature for 15 minutes in the dark. By dispensing 2 N sulfuric acid at 100 µL/well, the reaction was stopped, and the absorbance at 490 nm/630 nm was measured for each well.

(4) Results

The results of the cTnI measurement under each pretreatment condition are shown in Table 1. It was found that, by performing the pretreatment, the signal intensity (absorbance) of each positive sample increases. In particular, it was found that, in cases where the pretreatment is carried out under the condition of pretreatment liquid 2 or 3, both the signal intensity and the S/N ratio increase compared to those under the untreated measurement condition.

TABLE 1

| | | Untreated | Pretreatment liquid 1 5% SDS 10 mM Tris 20 mM DEAET 25 mM EDTA | Pretreatment liquid 2 5% SDS 10 mM Tris 20 mM DEAET — | Pretreatment liquid 3 5% SDS — 20 mM DEAET 25 mM EDTA |
|---|---|---|---|---|---|
| Serum sample A (2.3 ng/mL) | Absorbance | 0.096 | 0.131 | 0.157 | 0.141 |
| | Measured value/Blank value | 11.9 | 6.4 | 17.4 | 11.8 |
| | Pretreated/Untreated | — | 137% | 164% | 148% |
| Serum sample B (7.74 ng/mL) | Absorbance | 0.064 | 0.138 | 0.165 | 0.158 |
| | Measured value/Blank value | 8.0 | 5.1 | 18.3 | 13.2 |
| | Pretreated/Untreated | — | 216% | 258% | 247% |
| Blank | Absorbance | 0.008 | 0.018 | 0.009 | 0.012 |

Example 2 Test for Confirmation of Effect of SDS Pretreatment (2)

Seven serum samples with known cTnI concentrations were subjected to measurement by the same method as in Example 1 except that the pretreatment liquid was pretreatment liquid 4 in Table 2. The measurement results are shown in Table 2.

TABLE 2

| | | Untreated | Pretreatment liquid 4 5% SDS 20 mM DEAET 2 mM EDTA |
|---|---|---|---|
| Serum sample A (cTnI 2.3 ng/mL) | Absorbance | 0.05 | 0.072 |
| | Pretreated/Untreated | — | 144% |
| Serum sample C (cTnI 2.75 ng/mL) | Absorbance | 0.163 | 0.233 |
| | Pretreated/Untreated | — | 143% |
| Serum sample D (cTnI 5.34 ng/mL) | Absorbance | 0.128 | 0.236 |
| | Pretreated/Untreated | — | 184% |
| Serum sample E (cTnI 6.01 ng/mL) | Absorbance | 0.095 | 0.164 |
| | Pretreated/Untreated | — | 173% |
| Serum sample B (cTnI 7.74 ng/mL) | Absorbance | 0.098 | 0.237 |
| | Pretreated/Untreated | — | 242% |
| Serum sample F (cTnI 8.77 ng/mL) | Absorbance | 0.109 | 0.23 |
| | Pretreated/Untreated | — | 211% |
| Serum sample G (cTnI 12.76 ng/mL) | Absorbance | 0.084 | 0.26 |
| | Pretreated/Untreated | — | 310% |

Example 3 Confirmation of Specificity of SDS Pretreatment/Measurement System

Four serum samples with known concentrations were subjected to the same test as in Example 2 except that 20 µg/mL anti-cTnI antibody 19C7 (Hytest) was added to the primary reaction system, and that 10 µg/mL unlabeled anti-cTnI antibody 16A11 was added to the secondary reaction system (inhibition test). Comparison of the measurement result for each condition with the result of Example 2 is shown in Table 3. In the inhibition test, it could be confirmed that all samples show inhibitions of more than 95% also in the cases where the pretreatment was carried out. Thus, the measurement system could be confirmed to have specificity.

TABLE 3

| | Untreated | | | Pretreated | | |
|---|---|---|---|---|---|---|
| | No inhibition | With inhibition | Inhibition rate | No inhibition | With inhibition | Inhibition rate |
| Serum sample A (cTnI 2.3 ng/mL) | 0.052 | 0.001 | 97% | 0.077 | 0.003 | 96% |
| Serum sample B (cTnI 7.74 ng/mL) | 0.098 | 0 | 100% | 0.237 | 0.004 | 98% |
| Serum sample D (cTnI 5.34 ng/ml) | 0.128 | 0 | 100% | 0.236 | 0.006 | 97% |
| Serum sample F (cTnI 8.77 ng/mL) | 0.108 | 0 | 100% | 0.238 | 0 | 100% |

Example 4 Confirmation of Effect of Acidification Pretreatment: ELISA (1) Preparation of Anti-cTnI Antibody Plate To a polystyrene 96-well microwell plate (manufactured by Nunc), an antibody dilution solution (0.1 M sodium hydrogen carbonate, pH 9.6) containing 2 µg/mL anti-cTnI antibody 24F9 (manufactured by Fujirebio Inc.; which recognizes the 37th to 60th amino acid residues of cTnI) was dispensed at 100 µL/well, and the plate was then incubated at 4° C. overnight. The microwell plate was washed with PBS three times, and then a blocking liquid (PBS containing 0.5% casein sodium, 2% sucrose, and 0.05% ProClin (registered trademark) 300) was dispensed at 350 µL/well, followed by incubation at room temperature for not less than 2 hours. After removing the blocking liquid, the plate was dried to provide an anti-cTnI antibody plate.

(2) Measurement of cTnI

Seventy microliters of each of three serum samples with known cTnI concentrations or a blank (serum from a healthy individual) was mixed with 70 µL of pretreatment liquid 5 (0.83M urea, 0.14 N hydrochloric acid, 0.25% Triton X-100 (trade name), 0.07% C18TAB, 0.17% C16APS, 0.02% CHAPS, 83.3 mM imidazole, 20 mM DEAET), and the resulting mixture was warmed at 37° C. for 5 minutes to prepare an acidification-pretreated sample. In addition, 70 µL of each of the same samples was mixed with 70 µL of PBS, and similarly warmed to provide an untreated sample. The cTnI concentration in the serum sample was preliminarily measured using Centaur manufactured by Siemens.

To the anti-cTnI microwell plate, 25 µL of a buffer (0.6 M bicine, 2% sucrose, mM EDTA 2Na, 2% BSA, Proclin (registered trademark) 300, NaOH (about pH 9.2)) was dispensed, and then 75 µL of each of the samples (acidification-pretreated, untreated) was added thereto, followed by mixing the resulting mixture. For the untreated sample, a buffer at pH 7.0 was used. After incubation with shaking at 37° C. for 1 hour, washing was carried out five times with a washing liquid (0.05% Tween 20 (trade name)/PBS). A buffer containing 1 µg/mL biotinylated anti-cTnI antibody 16A11 (Hytest Inc.) was dispensed at 100 µL/well, and the reaction was allowed to proceed with shaking at 37° C. for 1 hour (secondary reaction). After five times of washing with the washing liquid, a labeled antibody liquid prepared by 10,000-fold dilution of HRP-labeled streptavidin (manufactured by Roche) with the buffer was dispensed at 100 µL/well, and the reaction was allowed to proceed with shaking at room temperature for 30 minutes. After five times of washing with the washing liquid, OPD substrate liquid (manufactured by Sigma) was dispensed at 100 µL/well, and the plate was left to stand at room temperature for 15 minutes in the dark. By dispensing 2 N sulfuric acid at 100 µL/well, the reaction was stopped, and the absorbance at 490 nm/630 nm was measured for each well.

The results of measurement of cTnI in the samples are shown in Table 4. It was found that, by performing the acidification pretreatment, the signal intensity (absorbance) of each positive sample increases.

TABLE 4

|  |  | Untreated | Pretreatment liquid 5 |
|---|---|---|---|
| Serum sample F (cTnI 2.0 ng/mL) | Absorbance | 0.010 | 0.046 |
|  | Pretreated/Untreated | — | 444% |
| Serum sample G (cTnI 6.01 ng/mL) | Absorbance | 0.014 | 0.152 |
|  | Pretreated/Untreated | — | 1052% |
| Serum sample H (cTnI 7.74 ng/mL) | Absorbance | 0.020 | 0.209 |
|  | Pretreated/Untreated | — | 1024% |
| Blank | Absorbance | 0.006 | 0.008 |
|  | Pretreated/Untreated | — | 133% |

Example 5 Confirmation of Effect of Acidification Pretreatment: CLEIA

Preparation of cTnI Measurement Reagent

Antibody-bound particle solution (immobilized antibody solution): antibody-bound magnetic particles in which an anti-cTnI antibody 24F9 is bound to carboxylated magnetic particles (manufactured by Fujirebio Inc.) were suspended in a buffer (36 mM potassium dihydrogen phosphate, 114 mM dipotassium hydrogen phosphate, 2.5% BSA, 0.05% casein sodium, 1.5% Triton X-100 (trade name), 0.1 M sodium chloride, 20 mM EDTA 2Na, 0.1% Proclin (registered trademark) 300; pH 7.0) at a concentration of 0.025% (w/v), to prepare an antibody-bound particle solution.

Labeled antibody solution: a labeled antibody obtained by labeling an anti-cTnI antibody 16A11 (Hytest Inc.) with alkaline phosphatase (highly active, sugar-reduced recombinant; manufactured by Roche) was diluted to 0.5 µg/mL with a labeled-substance diluent (50 mM MES, 2.5% (w/v) BSA, 100 mM NaCl, 0.3 mM $ZnCL_2$, and 1.0 mM $MgCl_2$; pH6.8), to prepare a labeled antibody solution.

These solutions were filled into special reagent bottles for an automatic immunoassay device Lumipulse Presto (manufactured by Fujirebio Inc.), and placed at prescribed positions.

(2) Acidification Pretreatment of Samples

Sixty seven microliters of each of 16 serum samples was mixed with 134 µL of pretreatment liquid 6 (0.83M urea, 0.14 N hydrochloric acid, 0.25% Triton X-100 (trade name), 0.07% C18TAB, 0.17% C16APS, 0.02% CHAPS, 83.3 mM imidazole, 20 mM DEAET), and the resulting mixture was warmed at 37° C. for 5 minutes. Thereafter, 101 µL of a neutralization liquid (0.6 M bicine, 2% sucrose, 10 mM EDTA 2Na, 2% BSA, 200 mM NLS, Proclin (registered trademark) 300, 1 N NaOH (about pH 9.2)) was added to the mixture, and the resulting mixture was mixed to prepare an acidification-pretreated sample.

(3) Measurement of Amount of cTnI

Using an automatic immunoassay device (Lumipulse Presto, manufactured by Fujirebio Inc.), the amount of cTnI in the acidification-pretreated sample was measured according to the following procedure.

In a reaction cuvette, 50 µL of the antibody-bound particle solution and 100 µL of the acidification-pretreated sample were dispensed to prepare a first reaction liquid. The first reaction liquid was stirred and then incubated at 37° C. for 8 minutes to allow formation of an immune complex of the anti-cTnI antibody bound to the magnetic particles and the cTnI antigen contained in the sample.

After the incubation, the magnetic particles were collected onto the tube wall using a magnet, and substances unbound to the magnetic particles were removed. Thereafter, injection of a washing liquid (Lumipulse (registered trademark) washing liquid, manufactured by Fujirebio Inc.) and removal of the washing liquid were repeated to wash the magnetic particles.

After the washing, 50 µL of the labeled antibody solution was mixed with the magnetic particles to prepare a second reaction liquid. The second reaction liquid was incubated at 37° C. for 8 minutes to allow formation of an immune complex constituted by the anti-cTnI antibody-cTnI antigen-labeled antibody, immobilized on the magnetic particles.

After the incubation, the magnetic particles were collected again onto the tube wall using a magnet, and substances unbound to the magnetic particles were removed. Thereafter, injection of the washing liquid and removal of the washing liquid were repeated to wash the magnetic particles.

To the magnetic particles, 200 µL of a substrate liquid containing AMPPD (3-(2'-spiroadamantane)-4-methoxy-4-(3'-phosphoryloxy)phenyl-1,2-dioxetane disodium salt) (Lumipulse (registered trademark) substrate liquid, manufactured by Fujirebio Inc.) was added, and the resulting mixture was stirred, followed by incubation at 37° C. for 4 minutes. The AMPPD contained in the substrate liquid was degraded by catalytic action of the alkaline phosphatase indirectly bound to the magnetic particles, to release light having an emission maximum at a wavelength of 477 nm. Since the luminescence intensity reflects the amount of cTnI bound to the magnetic particles, the amount of cTnI can be measured by measuring the luminescence intensity (counts) at a wavelength of 477 nm.

(4) Comparison with Measured Values Obtained with Commercially Available Reagent In addition, the 16 serum samples subjected to the measurement by the above-described method were subjected to measurement of cTnI using a commercially available reagent according to the description in the attached document. The measured value obtained with the commercially available reagent and the measured value (counts) obtained by the above method described in (1) to (3) for each sample are shown in Table 5 and FIG. 1. For most samples, the measured value of cTnI showed good correlation between the method of the present invention and the commercially available reagent. However, there were two samples that showed remarkably high measured values in the method of the present invention (Nos. 15 and 16).

TABLE 5

| Sample No. | Commercially available reagent Measured value (pg/mL) | Luminescence intensity (counts) |
|---|---|---|
| 1 | 180 | 2234 |
| 2 | 500 | 3208 |
| 3 | 4000 | 25871 |
| 4 | 220 | 997 |
| 5 | 460 | 2517 |
| 6 | 850 | 4688 |
| 7 | 8970 | 21031 |
| 8 | 9990 | 37315 |
| 9 | 11870 | 48468 |
| 10 | 13790 | 66238 |
| 11 | 16970 | 61841 |
| 12 | 29790 | 118636 |
| 13 | 33890 | 145771 |
| 14 | 2020 | 18581 |
| 15 | 3600 | 97078 |
| 16 | 260 | 27091 |

Example 6 Analysis of Deviated Sample by Gel Filtration Chromatography (1) Gel Filtration Chromatography of Deviated Sample Sample No. 16 in Example 5, for which the acidifier-pretreated sample showed a measured value deviated toward the high-value side from the correlation curve with the commercially available reagent, was analyzed using gel filtration chromatography in order to elucidate the cause of the elevation of the value.

By mixing 50 μL of a filtered gel filtration buffer (50 mM PB, 0.05% Tween 20, 0.08% CHAPS, 300 mM NaCl, 1 mM EDTA; pH6.0) with 150 μL of a filtered sample, and further adding 14 μL of a filtered protease inhibitor thereto, a gel filtration sample was prepared. The whole sample was applied to a gel filtration column, and separation was carried out under the following conditions.

(Separation Conditions)

Column: Superdex 200 10/30

Separation buffer: 50 mM PB, 0.05% Tween 20, 0.08% CHAPS, 300 mM NaCl, 1 mM EDTA; pH6.0

Flow rate: 0.5 mL/minute

Collection range: 6 to 23 mL; total, 34 fr. (0.5 mL/fraction)

(2) Recovery Test of TnI Solution with Known Concentration

Figure 2:
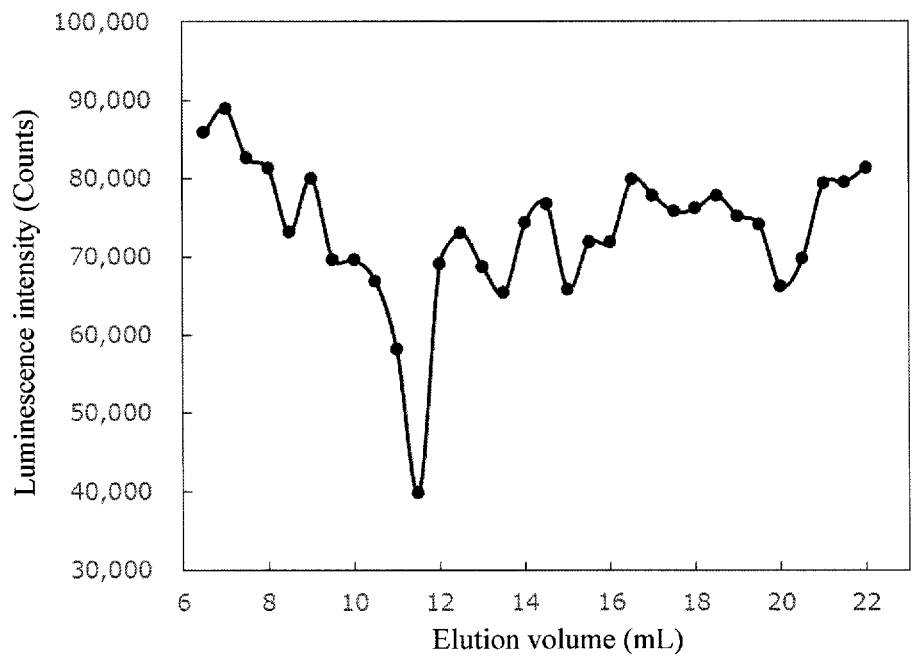
FIG. 2 is a diagram showing the influence, on detection of cardiac troponin I, of each fraction of gel filtration chromatography of a sample that showed a high value in the measurement method of the present invention using acidification pretreatment.

To 100 μL of each collected fraction, 80 μL of 1.125 ng/mL native troponin I (TnI) solution was added to prepare a sample for measurement of the recovery rate. By the same method as in Example 5 except that the antibody to be immobilized on the magnetic particles was 19C7 instead of 24F9, an antibody-bound particle solution and a labeled antibody solution were prepared, and each fraction of the sample for measurement of the recovery rate was subjected to measurement of cTnI under the same conditions as in Example 5 using Lumipulse Presto. The measurement result (luminescence intensity (counts)) for each fraction is shown in FIG. 2. It was shown that, in the untreated sample No. 16, a substance that remarkably inhibits the reaction between native TnI and 19C7 antibody is present in the eluted fraction near 11.5 mL. Based on the elution volume, reactivity with an anti-human IgG antibody, and the like, this inhibitor was suggested to be human anti-cTnI antibody (autoantibody).

The cTnI measurement method using the commercially available reagent, which was carried out for comparison in Example 5, is a system for measurement of native TnI which does not include a step of pretreatment of the sample or the like. There is thus a possibility that, in the measurement of sample No. 16, the value was lower than the actual amount of cTnI due to influence of the above inhibitor. On the other hand, the method of the present invention simplifies cTnI by the pretreatment of the sample, and therefore the influence of the inhibitor that specifically inhibits the reaction with native TnI (which is assumed to be autoantibody) can be avoided. This is assumed to be the reason why the measured value of cTnI was high, leading to the deviation toward the high-value side from the correlation curve with the commercially available reagent.

Example 7 Optimum Concentration of Acidifier

The optimum concentration of the acidifier to be used for the acidification pretreatment was studied. Seven kinds of pretreatment agents were prepared by the same method as in Example 5 except that the hydrochloric acid concentration was one of 0.03, 0.05, 0.06, 0.125, 0.25, 0.28, and 0.5 N. The neutralization liquid for each pretreatment agent was prepared by the same method as in Example 5 except that the pH was adjusted such that the pH after mixing with the pretreatment liquid became 7.5±0.2.

Native TnI, and two serum samples (Nos. 17 and 18) with known cTnI concentrations were diluted with PBS such that the cTnI concentration became 2250 pg/mL. Subsequently, each sample was subjected to acidification pretreatment by the same method as in Example 5 using each of the seven kinds of pretreatment liquids and the corresponding neutralization liquid. Each acidification-pretreated sample was subjected to measurement of the luminescence intensity (counts) corresponding to the amount of cTnI using Lumipulse Presto by the same method as in Example 5. The same treatment and measurement were carried out using PBS instead of the native TnI and the samples described above, to provide blanks. The count value for each sample was divided by the count value for the corresponding blank to calculate the S/N ratio.

Figure 3:
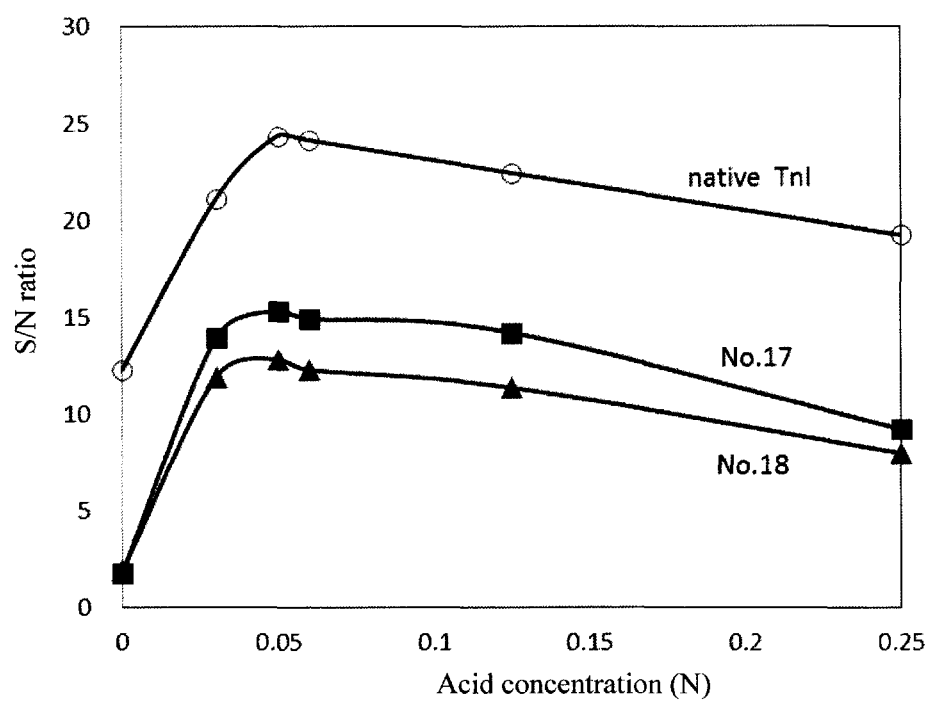
FIG. 3 is a diagram showing the relationship between the acid concentration of the pretreatment liquid and the measured value in the measurement method of the present invention using acidification pretreatment.

Table 6 and FIG. 3 show the S/N ratios obtained under the various acid treatment conditions.

TABLE 6

| Acid concentration (N) | Native TnI | No. 17 | No. 18 |
|---|---|---|---|
| 0 | 12.3 | 1.8 | 1.9 |
| 0.03 | 21.1 | 13.9 | 11.9 |
| 0.05 | 24.4 | 15.3 | 12.8 |
| 0.06 | 24.1 | 14.9 | 12.3 |
| 0.125 | 22.4 | 14.2 | 11.4 |
| 0.25 | 19.2 | 9.2 | 7.9 |
| 0.28 | 19.8 | 11.6 | 9.2 |
| 0.5 | 19.4 | 10.2 | 8.2 |

In the present Example, the acidification pretreatment had an effect of increasing the S/N ratio under the conditions in which the acid concentration was more than 0 N and not more than 0.5N. With the acid concentrations of 0.03 N to 0.125 N, particular increases in the S/N ratio were found.

The present inventors confirmed that the anti-cTnI antibody 24F9 used in the present Example reacts more strongly with simple cTnI than with native TnI (data not shown). On the other hand, it was confirmed that, although the commercially available anti-cTnI antibody 19C7 also reacts with simple cTnI, it reacts more strongly with native TnI (data not shown). In cases where an antibody such as 19C7 is used, although the effect of avoiding the influence of the inhibitor can be obtained by the acidification pretreatment, this effect could be canceled by the simplification of cTnI. It is assumed that, in cases where an antibody such as 24F9 is used, the acidification pretreatment produces not only the effect of avoiding the influence of the inhibitor, but also the positive action due to the simplification of cTnI, leading to a remarkable increase in the measured value even at a low acid concentration.

The invention claimed is:

1. A method of measuring, by immunoassay, human cardiac troponin I in a sample separated from a body, the method comprising a pretreatment step of mixing the sample separated from a body with a pretreatment liquid containing an acidifier or an anionic surfactant, wherein interaction by an autoantibody is avoided and wherein when the pretreatment liquid contains an acidifier, the pretreatment liquid further contains a cationic surfactant and wherein the method further comprises a step of mixing the liquid after the pretreatment step with a buffer containing a water-soluble polymer.

2. The method according to claim 1, wherein the pretreatment liquid further contains a reducing agent.

3. The method according to claim 1 or 2, wherein the pretreatment liquid contains an acidifier.

4. The method according to claim 1 or 2, wherein the pretreatment liquid contains an anionic surfactant.

5. The method according to claim 3, wherein the pretreatment step is carried out under heat.

6. The method according to claim 1, wherein the pretreatment liquid contains an acidifier, and the acidifier has a final concentration of more than 0.03 N and not more than 0.125 N in the pretreatment step.

7. The method according to claim 4, wherein the pretreatment step is carried out under heat.

8. A method of measuring, by immunoassay, human cardiac troponin I in a sample separated from a body, the method comprising a pretreatment step of mixing the sample separated from a body with a pretreatment liquid containing an acidifier, wherein interaction by an autoantibody is avoided and wherein the pretreatment liquid further contains a reducing agent or a cationic surfactant and wherein the method further comprises a step of mixing the liquid after the pretreatment step with a buffer containing a water-soluble polymer.

9. The method according to claim 8, wherein the pretreatment liquid further contains a reducing agent.

10. The method according to claim 8, wherein the pretreatment step is carried out under heat.

11. The method according to claim 8, wherein the pretreatment liquid said acidifier has a final concentration of more than 0.03 N and not more than 0.125 N in the pretreatment step.

\* \* \* \* \*